(12) United States Patent
Burkhoff

(10) Patent No.: US 10,744,255 B2
(45) Date of Patent: Aug. 18, 2020

(54) CARDIAC SUPPORT SYSTEM AND METHODS

(71) Applicant: HeartWare, Inc., Miami Lakes, FL (US)

(72) Inventor: Daniel Burkhoff, New York, NY (US)

(73) Assignee: HeartWare, Inc., Miami Lakes, FL (US)

(*) Notice: Subject to any disclaimer, the term of this patent is extended or adjusted under 35 U.S.C. 154(b) by 0 days.

(21) Appl. No.: 14/806,228

(22) Filed: Jul. 22, 2015

(65) Prior Publication Data

US 2016/0022896 A1 Jan. 28, 2016

Related U.S. Application Data

(60) Provisional application No. 62/027,512, filed on Jul. 22, 2014.

(51) Int. Cl.
*A61M 1/36* (2006.01)
*A61M 1/12* (2006.01)
(Continued)

(52) U.S. Cl.
CPC ........ *A61M 1/3621* (2013.01); *A61M 1/3659* (2014.02); *A61M 1/3666* (2013.01); *A61M 1/3667* (2014.02); *A61M 1/10* (2013.01); *A61M 1/1006* (2014.02); *A61M 1/1008* (2014.02); *A61M 1/1086* (2013.01); *A61M 1/12* (2013.01); *A61M 1/1698* (2013.01);
(Continued)

(58) Field of Classification Search
CPC .............. A61M 1/3621; A61M 1/1006; A61M 1/1008; A61M 1/3659; A61M 1/12; A61M 1/1086; A61M 1/1698; A61M 1/3666

See application file for complete search history.

(56) References Cited

U.S. PATENT DOCUMENTS 4,927,407 A 5/1990 Dorman
7,699,586 B2 4/2010 LaRose et al.
(Continued)

FOREIGN PATENT DOCUMENTS

CN 1220534 C 9/2005
CN 1747762 A 3/2006
(Continued)

OTHER PUBLICATIONS

Schwinger et al, The anatomy of the interatrial septum: a transesophageal echocardiographic study, Am Heart J., 1990, Jun. 119(6): 1401-5.*
(Continued)

*Primary Examiner* — Scott M. Getzow
(74) *Attorney, Agent, or Firm* — Christopher & Weisberg, P.A.

(57) ABSTRACT

A system and methods of using a multi-lumen catheter and a blood pump to increase cardiac output and blood oxygenation are described. The system diverts deoxygenated blood from the right atrium to the left atrium, through the atrial septum. The catheter is adapted for simultaneously pumping blood to and from a patient's heart. A gas exchanger may be used as part of the system to remove $CO_2$ and add $o_2$ to the blood that is pumped via the system. Components or portions of the system may be implantable in the patient.

7 Claims, 4 Drawing Sheets

(51) Int. Cl.
  *A61M 1/10* (2006.01)
  *A61M 1/16* (2006.01)
(52) U.S. Cl.
  CPC ..... *A61M 2205/04* (2013.01); *A61M 2205/33* (2013.01); *A61M 2205/3303* (2013.01); *A61M 2230/202* (2013.01); *A61M 2230/205* (2013.01)

(56) References Cited

U.S. PATENT DOCUMENTS

| | | | |
|---|---|---|---|
| 7,896,832 | B2 | 3/2011 | Zafirelis et al. |
| 7,972,122 | B2 | 7/2011 | LaRose et al. |
| 8,007,254 | B2 | 8/2011 | LaRose et al. |
| 8,394,010 | B2* | 3/2013 | Farnan ............... A61M 1/3653 600/16 |
| 9,011,311 | B2 | 4/2015 | Strueber |
| 2002/0057989 | A1 | 5/2002 | Afzal et al. |
| 2003/0069468 | A1* | 4/2003 | Bolling .................. A61M 1/10 600/16 |
| 2004/0052681 | A1 | 3/2004 | Mortensen et al. |
| 2004/0102732 | A1* | 5/2004 | Naghavi ................ A61M 1/16 604/29 |
| 2006/0100565 | A1* | 5/2006 | Aboul-Hosn ....... A61M 1/3653 604/9 |
| 2006/0245959 | A1 | 11/2006 | LaRose et al. |
| 2006/0284423 | A1 | 12/2006 | Katsuno et al. |
| 2007/0161845 | A1 | 7/2007 | Magovern et al. |
| 2010/0185136 | A1 | 7/2010 | Thomas |
| 2011/0160518 | A1 | 6/2011 | Zafirelis et al. |
| 2011/0190683 | A1 | 8/2011 | Gellman et al. |
| 2011/0230821 | A1 | 9/2011 | Babic |
| 2012/0302995 | A1 | 11/2012 | Hochareon |
| 2014/0012066 | A1 | 1/2014 | Aboul-Hosn et al. |
| 2015/0182681 | A1 | 7/2015 | Strueber |

FOREIGN PATENT DOCUMENTS

| | | |
|---|---|---|
| CN | 101415452 A | 4/2009 |
| WO | 8702894 A2 | 5/1987 |
| WO | 2005/037345 A2 | 4/2005 |
| WO | 2006031858 A1 | 3/2006 |

OTHER PUBLICATIONS

Extended European Search Report for Application No. EP13772625 dated Oct. 27, 2015.

International Search Report and Written Opinion for Application No. PCT/US2015/041598 dated Oct. 30, 2015.

International Search Report issued by the International Searching Authority (ISA/US) dated Jun. 26, 2013 in connection with International Application No. PCT/US2013/035484.

Written Opinion of the International Searching Authority issued by the International Searching Authority (ISA/US) dated Jun. 26, 2013 in connection with International Application No. PCT/US2013/035484.

Zhang et al., "A novel wearable pump-lung device: In vitro and acute in vivo study," J. of Heart & Lung Transplantation (Aug. 22, 2011) pp. 101-105.

Notice on the First Office Action and Search Report, China National Intellectual Property Administration, dated Dec. 18, 2018 for corresponding Application No. 201580049690.2, with English Translation.

* cited by examiner

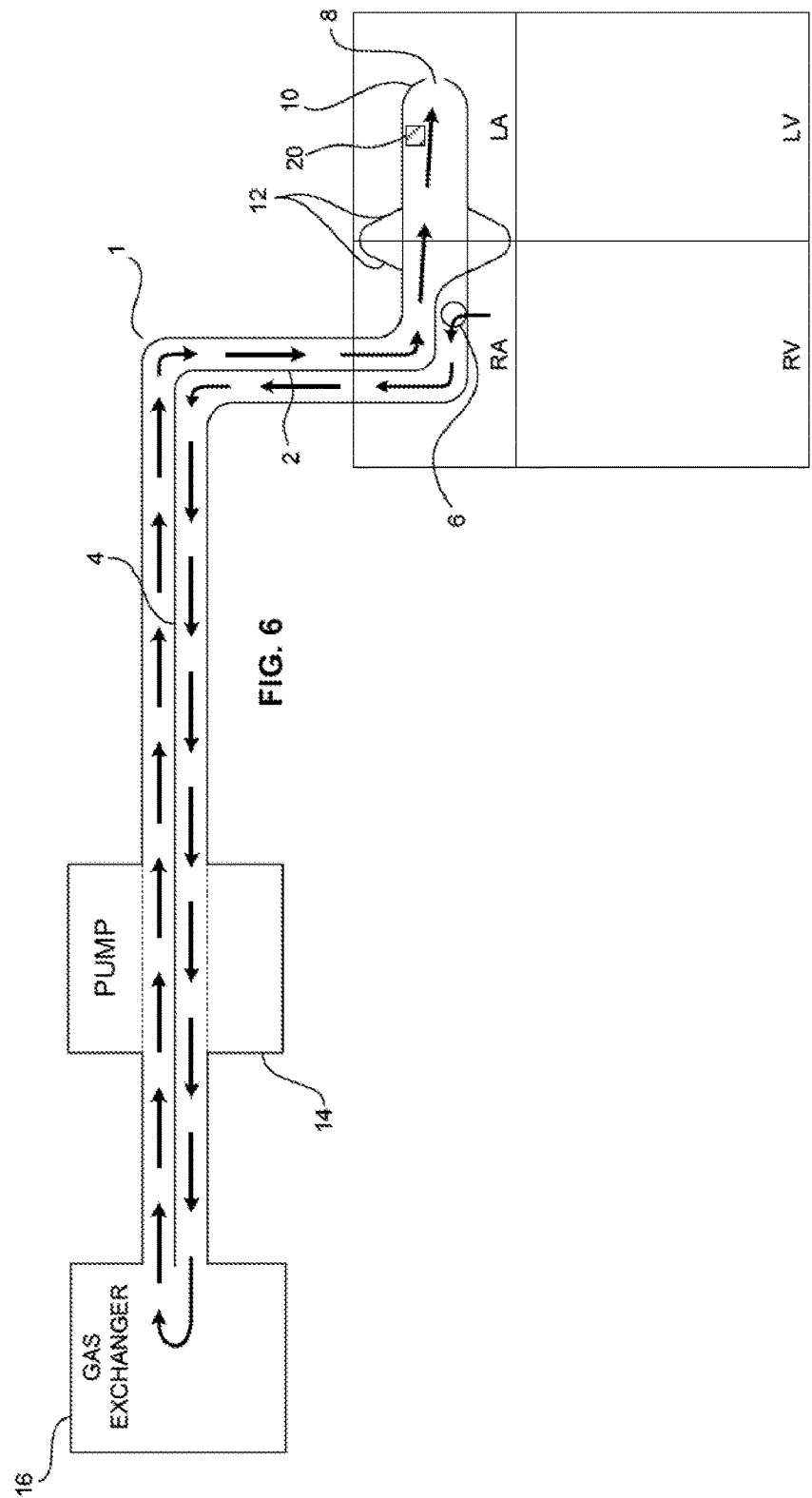

CARDIAC SUPPORT SYSTEM AND METHODS

CROSS REFERENCE TO RELATED APPLICATIONS

The present application claims the benefit of the filing date of U.S. Provisional Patent Application No. 62/027,512, filed Jul. 22, 2014, the disclosure of which is hereby incorporated herein by reference.

BACKGROUND OF THE INVENTION

Extracorporeal Membrane Oxygenation (ECMO is a treatment modality typically used in patients to replace or assist in the respiratory and/or cardiac function of medically compromised patients. In its broadest sense, ECMO uses one or more catheters and a pump system to draw blood away from the body, outside of the patient. The blood is then pumped through a gas exchanger, where carbon dioxide ($CO_2$) is removed from the blood and oxygen ($O_2$) is added. The oxygenated blood is then pumped back to the circulatory system of the patient, where it can be perfused to the rest of the body. In some ECMO systems, blood is drawn from the venous system and returned to the arterial system. In other forms, it is drawn from the venous system and returned to the venous system.

ECMO is usually implemented by large bore cannulae inserted percutaneously into a major peripheral vein or a major peripheral artery of the body (e.g., femoral vein, subclavian vein, jugular vein; femoral artery, subclavian artery, etc.). However, there are many patients in whom the right ventricle is not working properly and/or there is a major problem with the pulmonary circuit that renders this form of therapy ineffective.

SUMMARY OF THE INVENTION

The present invention includes systems and methods for improving total cardiac output in a patient, and which include a multi-lumen catheter. The multi-lumen catheter of the present invention has a proximal end and a distal end, an inflow opening communicating with a first lumen of the catheter, and an outflow opening communicating with a second lumen of the catheter, wherein the inflow opening is proximal to outflow opening. In certain embodiments, the first lumen may be shorter in length than the second lumen and the distal end of the first lumen is adapted to rest against the atrial septum. In further embodiments, a distal portion of the multi-lumen catheter may be covered in a sheath and the sheath may be removable by the physician.

An aspect of the present invention is directed to a method for improving total cardiac output of a patient comprising a) inserting a multi-lumen catheter through the atrial septum of the patient so that an inflow opening that is in fluid communication with a first lumen of the catheter is disposed within the right atrium, and an outflow opening in fluid communication with a second lumen of the catheter is disposed within the left atrium, and b) pumping deoxygenated blood from the right atrium to the left atrium through the catheter. The method may also include a catheter with a proximal end and a distal end, with the inflow opening proximal to the outflow opening. The inserting step may entail a minimally invasive step of advancing the distal end of the catheter through a vein through the right atrium, to the septum, and then further advancing the distal end through the septum.

The methods may be performed with or without extracorporeal gas exchange and may include mixing of the deoxygenated blood, with oxygenated blood in the left atrium. Such mixing may increase the total amount of oxygen delivered to the patient's tissue ($DO_2$).

The pumping of deoxygenated blood may also include drawing the deoxygenated blood into the inflow opening, through the first lumen, towards the pump. The pumping of deoxygenated blood may also include pumping blood through the second lumen, through the outflow opening, and into the patient's left atrium. This pumping of blood into the left atrium via the second lumen increases the volume of blood in the left atrium. The increased volume of blood in the left atrium increases the filling of the left ventricle. The pumping of deoxygenated blood may be done at a controlled flow rate. The flow rate may also be determined by the amount of left ventricular filling and/or the patient's $DO_2$. Pumping of deoxygenated blood away from the patient by way of the systems and methods of the present invention increases the patient's $DO_2$.

In other embodiments, the distal end of the catheter is anchored in the atrial septum of the patient. This anchoring may be accomplished via clamps located at the distal end of the catheter. The distal end of the catheter may also include at least one sensor to determine the amount of left ventricular filling. The catheter may be placed via percutaneous implantation methods.

Another aspect of the present invention is directed to a system for diverting deoxygenated blood from the right atrium to the left atrium, through the atrial septum. The system includes a multi-lumen catheter and a blood pump adapted for simultaneously pumping blood to and from a patient's heart. The pump and/or catheter may be configured to be surgically implanted in the patient. In some embodiments, the pump may be configured to be implantable in a subcutaneous pocket of a patient. In other embodiments, the pump and/or catheter are configured to be located external to the patient.

DESCRIPTION OF THE DRAWINGS

FIG. 6 is a schematic depiction of one embodiment of a dual lumen catheter implanted in a mammalian heart and also depicts a gas exchanger and the flow of blood from the right atrium (RA) through the pump and gas exchanger, and to the left atrium (LA).

DETAILED DESCRIPTION

The present invention is directed, in part to a method for improving total cardiac output and total oxygen delivery of a patient. Embodiments of the invention enable withdrawal of blood from the right atrium, or neighboring venous system, and delivery back to the left atrium. This can be useful in patients when it is desired to have the blood partially or completely bypass the right ventricle and lungs.

In this embodiment, the blood may be withdrawn from the body by a pump; it can then be oxygenated and returned (via the same pump) to the left atrium. This has applications for patients with isolated right heart failure, pulmonary edema, pulmonary hypertension, acute lung injury and other conditions. This arrangement is only one variation of ECMO.

Figure 1:
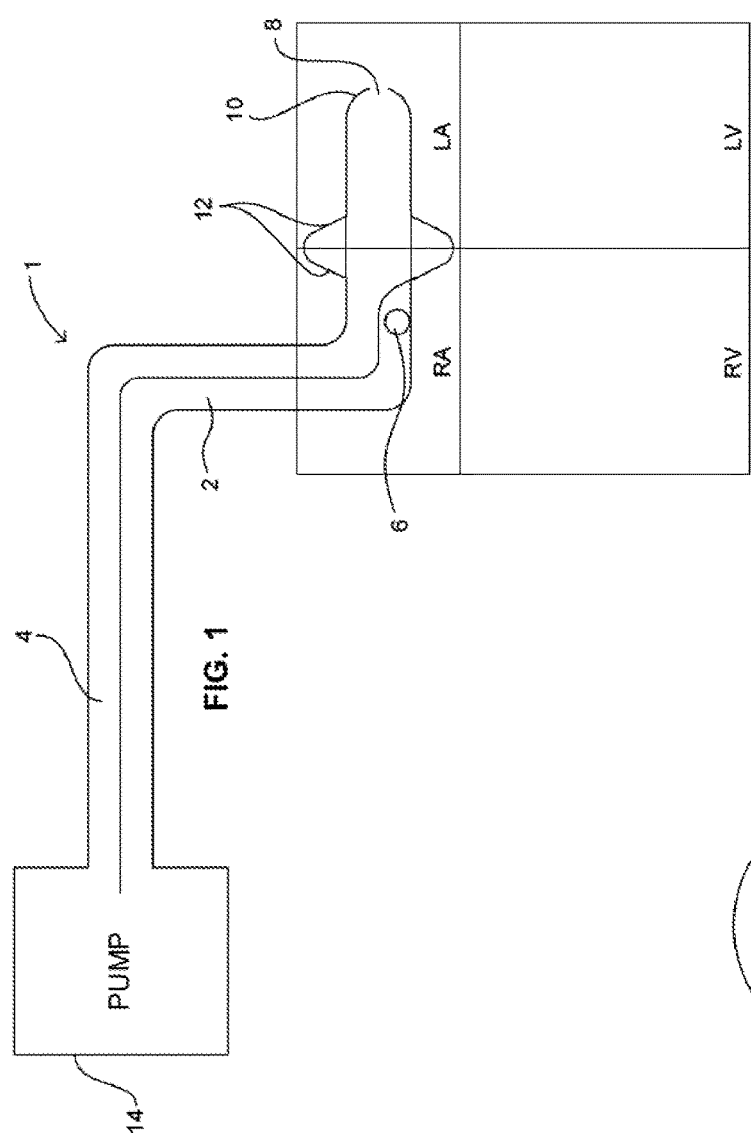
FIG. 1 is a schematic depiction of one embodiment of a dual lumen catheter implanted in a mammalian heart.

In one embodiment, as illustrated in FIG. 1, a multi-lumen catheter 1 is used to facilitate blood flow to and from a patient's heart. In the present invention, the multi-lumen catheter 1 may also be referred to as the catheter. The catheter 1 may also be configured for minimally invasive intravascular introduction into the heart, eliminating the need for open heart surgery. The multi-lumen catheter 1 may have a distal end located towards the patient and a proximal end located towards the pump. The multi-lumen catheter 1 may contain at least a first lumen 2 and a second lumen 4. The first and second lumens generally extend from the proximal end of the catheter to the distal end of the catheter. In one embodiment, the first and second lumens may be tubular in shape.

Figure 2:
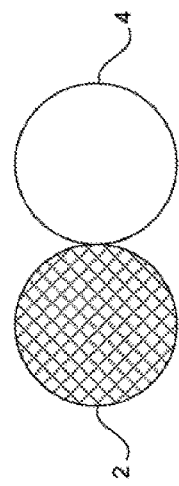
FIG. 2 is a cross sectional view of one embodiment of a dual lumen catheter.
Figure 3:
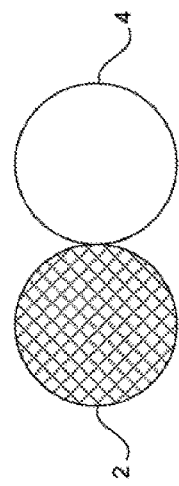
FIG. 3 is a cross sectional view of one embodiment of a dual lumen catheter.
Figure 5:
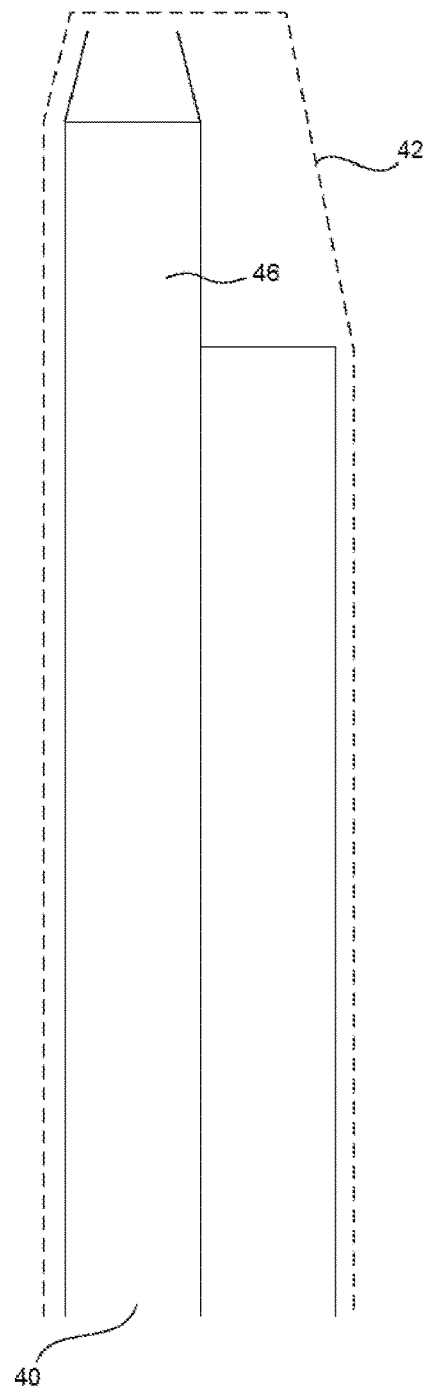
FIG. 5 is a schematic view of an additional embodiment of a dual lumen catheter.

In one embodiment, the first lumen 2 and second lumen 4 may be arranged in a coaxial configuration, wherein one lumen 2 is disposed within the other lumen 4, as shown in FIG. 2. In another embodiment, first lumen 2 and second lumen 4 may be arranged in a parallel configuration as shown in FIGS. 3 and 5, or the like. The distal end of the first lumen 2 may be sealed to prevent the backflow of blood from the first lumen to the second lumen. Additional lumens may also be included which allow for passage of guide wires or other devices (not shown). Such configurations are also described in the U.S. Pat. No. 8,394,010, which is fully incorporated herein.

Towards the distal end of the catheter, the first lumen 2 may be configured with an inflow opening 6. The inflow opening 6 may be an opening located in an outer wall of the first lumen. The distal end of the second lumen may also be configured with an outflow opening 8 at the end of the multi-lumen catheter 1, or in the sidewall of the second lumen (not shown), similar to the inflow opening 6 in the first lumen. As shown in FIG. 1, in one embodiment, the inflow opening 6 is proximal to the outflow opening 8.

The distal end of the catheter 1 may also be configured with a tip 10, which facilitates advancement of the multi-lumen catheter, through a vein, such as the femoral vein, and ultimately through the atrial septum of a patient. In one embodiment, the tip 10 may be pointed, rounded or tapered, which may facilitate advancement through the vascular path, into the left atrium. In a preferred embodiment, the tip 10 does not contain sharp edges, which minimizes the potential of trauma to the patient's tissue, upon insertion of the catheter 1.

The distal end of the catheter 1 may also be configured with one, or preferably two sets of anchor members 12. The anchor members may also be referred to herein as clamps. The anchor members 12 may function to secure or clamp the catheter in position within the atrial septum, and prevent the catheter from advancing too far into the patient's left atrium. The anchor members 12 may also prevent the catheter from pulling out of the left atrium, into the right atrium. Exemplary anchor members are described in detail in U.S. Pat. No. 8,394,010, referenced above.

Figure 4:
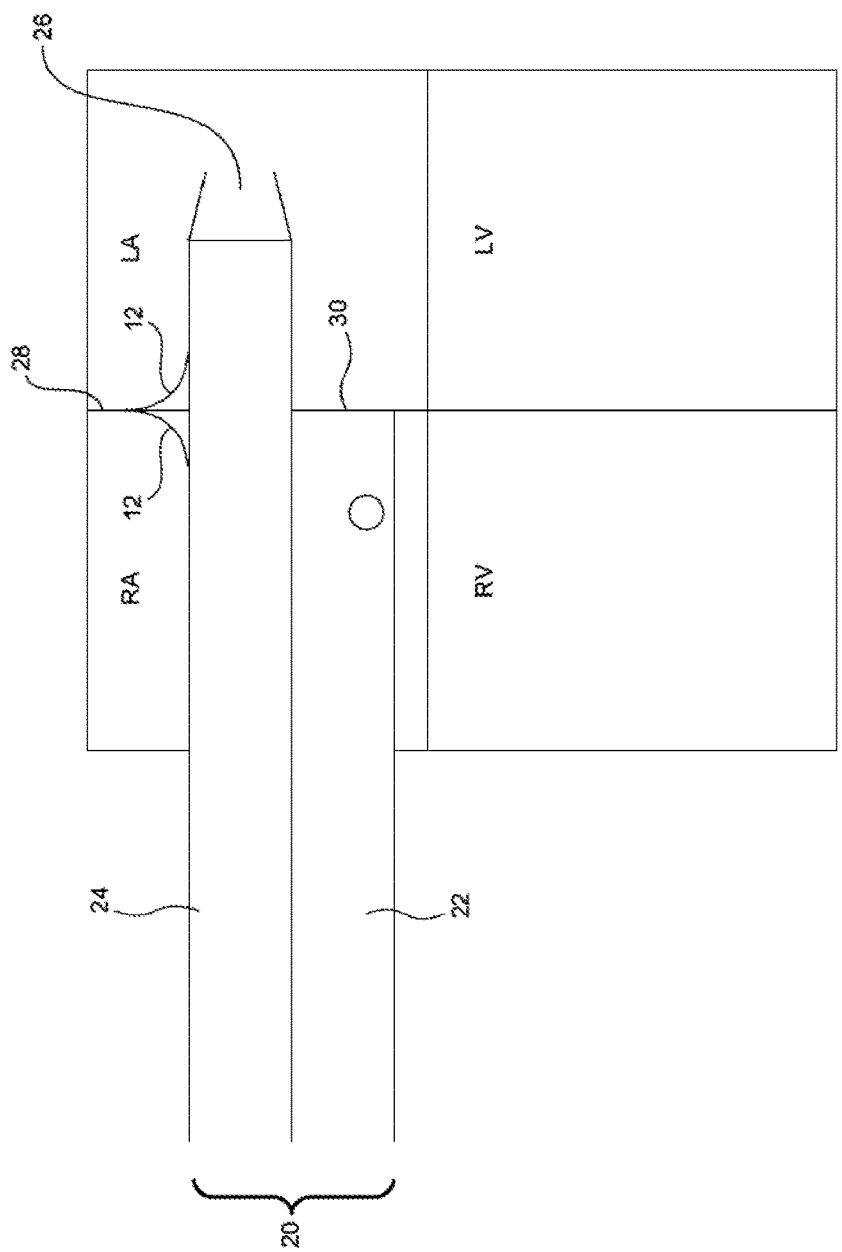
FIG. 4 is a schematic depiction of an alternative embodiment of a dual lumen catheter implanted in a mammalian heart.

In FIG. 4, another embodiment of a multi-lumen catheter 20 is shown. The multi-lumen catheter 20 has a first lumen 22 and a second lumen 24, arranged parallel to one another. In this embodiment, the first lumen 22 is shorter in length than the second lumen 24. This difference in length causes the second lumen 24 to extend further than the first lumen 22, at the distal end of the multi-lumen catheter 20. In this embodiment, as the distal tip 26 is advanced through the atrial septum 28 of a patient, the distal end 30 of the first lumen 22 will reside in the right atrium, against or near the atrial septum 28. The distal tip 26 will reside in the left atrium. This configuration may prevent the multi-lumen catheter 20 from advancing too far into the left atrium of the patient. In this embodiment, the multi-lumen catheter may also contain anchor members 12, as discussed above with respect to FIG. 1.

FIG. 5 shows another optional feature of a multi-lumen catheter 40, which shows a sheath or tip 42 placed over the outside of at least the distal portion of the multi-lumen catheter 40. The sheath or tip 42 may streamline the distal end of the multi-lumen catheter 40, and facilitate its advancement through the patient's vasculature and into the heart. It may also prevent the distal portion of the multi-lumen catheter 40 from getting caught by or damaging the patient's tissue. The sheath or tip 42 may be removable by the doctor after insertion of the second lumen 46 through the septum (not shown).

As shown in FIG. 6, another embodiment of the systems described herein may be combined with a blood pump 14 of any type known in the art, and/or an optional gas exchanger 16. The combination of a catheter, pump and/or gas exchanger 16, may be referred to herein as a cardiac support circuit. In a preferred embodiment, the cardiac support circuits may be fully or partially implantable in a patient. FIG. 6 also depicts the flow of blood from the right atrium, through the catheter and then to the left atrium.

In one embodiment, as illustrated in FIG. 1, the pump is attached to the proximal end of the catheter. In another embodiment, the cardiac support circuit may also be configured to attach to an external gas exchange device of the types commonly known to perform extra-corporeal membrane oxygenation (ECMO) (not shown).

In yet another embodiment, the cardiac support circuit may include various sensors, such as oxygen and carbon dioxide sensors. For example, an oxygen sensor 20 may be located at the distal end of the catheter. This positioning may allow the sensor to detect blood gas levels in the left atrium. In this embodiment, the cardiac support circuit may also contain electrical circuitry to transmit signals received from the sensor, to the pump. The sensors may also be configured to sense and determine the amount of atrial and/or ventricular filling.

The pump may be further configured to adjust its speed, flow rate and other parameters based, at least in part, on data signals received from the sensor(s).

Chronic Use with NO Gas Exchanger

The method of transporting blood to and from the patient's heart may be practiced without a gas exchanger. For example, as illustrated in FIG. 1 the first lumen 2 may transport blood from the right atrium of the heart towards a pump 14 attached to the multi-lumen catheter 1 and positioned along the flow path of blood. The second lumen 4 transports blood from the pump 14 back towards the patient's heart.

The cardiac support circuit may comprise a multi-lumen catheter 1 and a blood pump 14. The multi-lumen catheter 1 may be introduced through a peripheral vein and advanced towards the heart. The tip 10 of the multi-lumen catheter 1 may be passed through the superior vena cava, into the right atrium, and through an opening created in the atrial septum through a septostomy or similar procedure.

As shown in FIG. 1, when placed in accordance with this embodiment, the distal tip 10 of the multi-lumen catheter 1 will partially extend into the left atrium. Insertion of a minimal portion of the distal tip 10 of the catheter may reduce potential thrombus formation. In addition, inflow opening 6 may reside in the right atrium of the patient. Once placed through the septum, the anchor members 12 (if present) are engaged in order to secure the catheter in the septum.

After placement, deoxygenated blood may be pumped from the right atrium, through the inflow opening 6 into the first lumen 2. Once in the first lumen 2, the deoxygenated blood is pumped in a direction towards the pump 14. The blood may then exit the pump 14 through the second lumen 4, towards the heart. This deoxygenated blood then leaves the second lumen via the outflow opening 8, into the left atrium. The pumping of both deoxygenated and oxygenated blood may be done a controlled flow rate. The pump of the present invention may be adapted with the functionality to adjust the flow rate. The flow rate may be adjusted and programmed manually by the physician, or adjusted in real time based on physiological demands of the patient, determined in part by the sensors described herein. The flow rate may also be determined or influenced by the patients DO2, or the extent of ventricular filling. By way of example only, a decrease in DO2 may demand a higher flow rate. Similarly, a decrease in ventricular filling may demand a higher flow rate to compensate for the decreased filling.

This process may increase the volume of blood delivered to the left atrium and ultimately, the left ventricle. In this embodiment, deoxygenated blood pumped from the right atrium, into the left atrium may cause the blood to mix in the left atrium. While this blood mixing may decrease the oxygen level of the oxygenated blood in the left atrium, it may have also the beneficial effect of increasing the volume of blood and filling in the left ventricle. In patients with impaired left ventricular filling, the added blood volume, while deoxygenated, may nevertheless help to increase their cardiac output and the total amount of oxygen delivered to the tissue ($DO_2$).

This is illustrated in the following theoretical calculations demonstrating that active pumping of deoxygenated blood from vein to left atrium results in significant increase in total cardiac output (CO) at both rest and during exercise and is also expected to increase $DO_2$ under both conditions (other lines in the tables are used in the calculation of $DO_2$):

|  | Baseline | +VA Pumping | Units |
| --- | --- | --- | --- |
| AT REST |  |  |  |
| CO (LV) | 4 | 3.5 | L/min |
| Pump Flow | 0 | 2 | L/min |
| CO (Total) | 4 | 5.5 | L/min |
| Arterial $O_2$ Sat | 92 | 79.5 | % |
| Arterial $O_2$ Content | 16.5 | 14.2 | ml/dL |
| $DO_2$ | 660 | 781 | mlO2/min |
| $VO_2$ | 121.5 | 121.5 | ml/min/M2 |
|  | 211.8 | 211.8 | mlO2/min |
|  | 2.8 | 2.8 | mi/min/kg |
| Mixed venous $O_2$ return | 448.2 | 569.2 | mlo2/min |
| Mixed venous $o_2$ Content | 11.2 | 10.3 | ml/dL |
| Mixed venous saturation | 63 | 57.5 | % |
| EXERCISE |  |  |  |
| CO (LV) | 8 | 7.5 | L/min |
| Pump Flow | 0 | 2 | L/min |
| CO (Total) | 8 | 9.5 | L/min |

-continued

|  | Baseline | +VA Pumping | Units |
| --- | --- | --- | --- |
| Arterial $O_2$ Sat | 92 | 79.6 | % |
| Arterial $O_2$ Content | 16.5 | 14.2 | ml/dL |
| $DO_2$ | 1320 | 1349 | mlO2/min |
| $VO_2$ | 450.0 | 450.0 | ml/min/M2 |
|  | 784.3 | 784.3 | mlO2/min |
|  | 10.5 | 10.5 | ml/min/kg |
| mixed venous $O_2$ return | 535.7 | 564.7 | mlo2/min |
| venous Content | 6.7 | 5.9 | ml/dL |
| Mixed venous saturation | 38 | 33 | % |

In this embodiment, the cardiac support circuit may be configured for chronic use. Accordingly, the pump and multi-lumen catheter may be configured for implantation into a patient.

Chronic Use with a Plug and Play Gas Exchanger

In another embodiment, the cardiac support circuit may also be configured for use with a gas exchanger 16. The gas exchanger could be any type commonly known in the art that is used for ECMO. The gas exchanger may be a permanent part of the cardiac support circuit, or could be a "plug and play" type of exchanger. In other words, the cardiac support circuit may be equipped with a location and adapter to releasably receive a gas exchanger, if necessitated by the patient's condition. The gas exchanger may be adapted to remove $CO_2$ from the blood and add $O_2$, before the blood is returned back to the patient. In embodiments that also employ the use of various physiological sensors, such as an oxygen sensor, a hypoxic condition could trigger an alarm, indicating the need for the gas exchanger to be attached to the cardiac support circuit and activated.

In further embodiments, the oxygen sensor could trigger a cascade event in the gas exchanger. In such an event, the sensor would activate if hypoxia was detected in the patient. This sensor would transmit a signal to the gas exchanger that a hypoxic condition occurred or is occurring. That signal would activate the gas exchanger to increase the rate or quantity of gas exchange to compensate for the hypoxic condition. This cascade of events could occur in real time via a feedback loop, which could provide for constant and continuous monitoring of the blood gas levels within the patient. While this functionality is useful with any type of patient requiring the systems of the present invention, it could be particularly useful in patients who may have portable ECMO or LRT systems. These patients may be ambulatory and experience changes in $O_2$ and $CO_2$ levels depending on various factors, such as physical exertion. The described functionality would allow those patients to resume more normal activity, as the inventive systems could adjust their blood gas levels on demand, as needed.

This configuration could also be used in chronic situations, in which the pump and catheter are implanted. Traditional extracorporeal membrane oxygenation (ECMO) apparatuses are cumbersome and often require trained personnel to manage. The present invention thus presents an alternative, which allows the patient to have an implantable system, that could be worn at home and that does not require the same type of assistance from medical personnel required by traditional ECMO systems. In one embodiment, the pump may be implantable in a subcutaneous pocket in the patient. In such an embodiment, the subcutaneously implantable pump may also be configured with an external adapter to receive a gas exchanger.

The system as a whole may be adapted to releasably plug into a gas exchanger, should the need arise. An ECMO device could be attached in acute or chronic situations. For example, the ECMO device could have a pump and a gas exchanger. In one embodiment, the pump and oxygenator could hook up directly to the inflow and outflow ports of the cannula.

Acute Use-External Pump—any Type of Pump—with or without $O_2$.

In another embodiment, the multi-lumen catheter is configured for use in acute situations, in which the size of the pump and oxygenator and their ability to be implanted are not a concern. In such acute situations, the multi-lumen catheter could be placed in accordance with methods described above. However, the catheter could be attached to any available external pump and, if needed, a gas exchanger. This attachment functionality could be achieved by way of a universal adapter at the proximal end of the catheter. In these situations, the multi-lumen catheter could also be used with or without a gas exchanger for ECMO. In this embodiment, the catheter is positioned percutaneously and the proximal end of the catheter may also be configured with a universal adapter that is compatible with any blood pump.

Venous to Arterial Mixing

In yet another embodiment, blood may be pumped from a peripheral vein, such as the femoral vein, through a catheter, and into a peripheral artery, such as the femoral artery. This method could be practiced without a gas exchanger. This type of pumping may increase the total oxygen delivery and volume of blood in the artery of patients with cardiac insufficiency. This embodiment is not limited to any particular vasculature, and may be used in conjunction with other techniques, such as ECMO.

The methods and systems described herein are designed to increase the total cardiac output of a patient, as well as increase the blood gas exchange efficiency in patients with respiratory and cardiac insufficiency.

The invention claimed is:

1. A system for diverting deoxygenated blood from the right atrium to the left atrium, through the atrial septum comprising:
    a multi-lumen catheter and a blood pump configured to simultaneously pump blood to and from a patient's heart, the multi-lumen catheter having an implanted configuration including a proximal end and a distal end, an inflow opening communicating with a first lumen of the catheter proximate the distal end, and an outflow opening communicating with a second lumen of the catheter at the distal end, the first lumen and the second lumen being parallel and adjacent to each other and the catheter being sized so that the inflow opening is located in the right atrium and the outflow opening is located in the left atrium, the inflow opening being proximal to the outflow opening with the atrial septum disposed therebetween when the distal end of the catheter is positioned within the left atrium, the distal end of the catheter including a plurality of clamps being configured to clamp to opposite sides of the atrial septum, the distal end of first lumen being sealed to prevent backflow of blood from the first lumen to the second lumen; and
    a gas exchanger having the first lumen and the second lumen coupled thereto at the proximal end of the multi-lumen catheter, the first lumen and the second lumen being in fluid communication with the blood pump.

2. The system of claim 1, wherein the pump is configured to be surgically implanted in the patient.

3. The system of claim 1, wherein the pump is configured to be implanted in a subcutaneous pocket.

4. The system of claim 1, wherein the first lumen is shorter in length than the second lumen.

5. The system of claim 4, wherein a distal end of the first lumen is adapted to rest against the atrial septum.

6. The system of claim 5, wherein a distal portion of the multi-lumen catheter is covered in a sheath.

7. The system of claim 6, wherein the sheath is removable.

* * * * *